(12) United States Patent
Maruyama et al.

(10) Patent No.: US 8,747,838 B2
(45) Date of Patent: Jun. 10, 2014

(54) METHOD FOR ISOLATING SMOOTH MUSCLE STEM CELLS

(75) Inventors: Tetsuo Maruyama, Tokyo (JP); Masanori Ono, Tokyo (JP)

(73) Assignee: Keio University, Tokyo (JP)

( * ) Notice: Subject to any disclaimer, the term of this patent is extended or adjusted under 35 U.S.C. 154(b) by 273 days.

(21) Appl. No.: 12/937,305

(22) PCT Filed: Apr. 13, 2009

(86) PCT No.: PCT/JP2009/057809
§ 371 (c)(1),
(2), (4) Date: Oct. 11, 2010

(87) PCT Pub. No.: WO2009/125877
PCT Pub. Date: Oct. 15, 2009

(65) Prior Publication Data
US 2011/0033428 A1 Feb. 10, 2011

(30) Foreign Application Priority Data
Apr. 11, 2008 (JP) .................................. 2008-103867

(51) Int. Cl.
*A01N 63/00* (2006.01)

(52) U.S. Cl.
USPC .......................... 424/93.7; 435/7.21; 435/325

(58) Field of Classification Search
None
See application file for complete search history.

(56) References Cited

U.S. PATENT DOCUMENTS

2008/0194710 A1   8/2008   Wilson et al.

FOREIGN PATENT DOCUMENTS

| JP | 2007 202435 | 8/2007 |
|---|---|---|
| WO | WO 2005/113753 A2 | 12/2005 |
| WO | WO 2005/113753 A3 | 12/2005 |

OTHER PUBLICATIONS

Zannettino et al., Haematologica, 2007, vol. 92, No. 12, p. 1707-1708.*
Lawson et al., PNAS, 2007, vol. 104, No. 1, p. 181-186.*
International Search Report issued Jul. 14, 2009 in PCT/JP09/057809 filed Apr. 13, 2009.
Ono, M. et al., "Side Population in Human Uterine Myometrium Displays Phenotypic and Functional Characteristics of Myometrial Stem Cells", Proc. Natl. Acad. Sci. /PNAS/ vol. 104, No. 47, pp. 18700-18705 , 1/3-3/3 and 7 pages of drawings and tables, (Nov. 20, 2007).
Szotek, P. P. et al., "Adult Mouse Myometrival Label-Retaining Cells Divide in Response to Gonadotropin Stimulation", Stem Cells, vol. 25, pp. 1317-1325 and 2 pages of drawings, (2007).
Ono, M. et al., " Development of Novel Method for Separating Human Ulterine Smooth Muscle Stem Cell Using Surface Antigen and Role Thereof in Remodeling of Pregnant Uterus", Regenerative Medicine, The Journal of the Japanese Society for Regenerative Medicine, vol. 8, p. 187, Suppl. (Abstract 0-27-7) (Feb. 5, 2009) (with English translation).
Extended European Search Report issued Jul. 9, 2012, in Patent Application No. 09729768.3.
Carol S. Trempus, et al., "Enrichment for Living Murine Keratinocytes from the Hair Follicle Bulge with the Cell Surface Marker CD34", The Journal of Investigative Dermatology, vol. 120, No. 4, XP 003009211, Apr. 2003, pp. 501-511.
Grant A. Challen, et al., "A Side Order of Stem Cells: The SP Phenotype", Stem Cells, vol. 24, No. 1, XP 002562631, Jan. 1, 2006, pp. 3-12.
Shunichiro Tsuji, et al., "Side population cells contribute to the genesis of human endometrium", Fertility and Sterility, vol. 90, Suppl 2, XP 025479674, Oct. 2008, pp. 1528-1537.

* cited by examiner

*Primary Examiner* — Kade Ariani
(74) *Attorney, Agent, or Firm* — Oblon, Spivak, McClelland, Maier & Neustadt, L.L.P.

(57) ABSTRACT

This invention relates to a method for isolating smooth muscle stem cells derived from mammalian smooth muscle comprising bringing mammalian smooth muscle cells into contact with a fluorescence-labeled anti-CD45 antibody, anti-CD34 antibody, and anti-CD49f antibody, and isolating cells that would not bind to the anti-CD45 antibody but would bind to the anti-CD34 antibody and the anti-CD49f antibody.

17 Claims, 15 Drawing Sheets

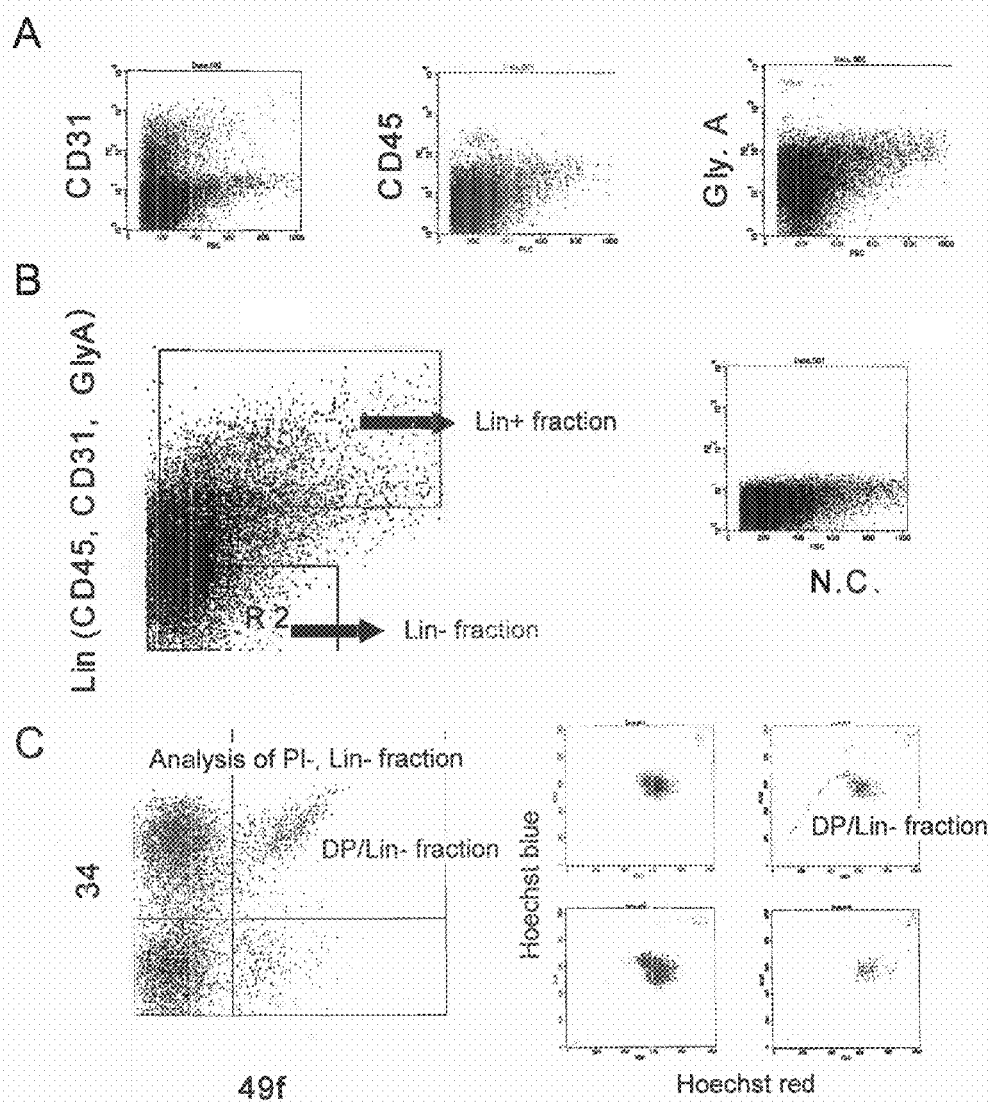

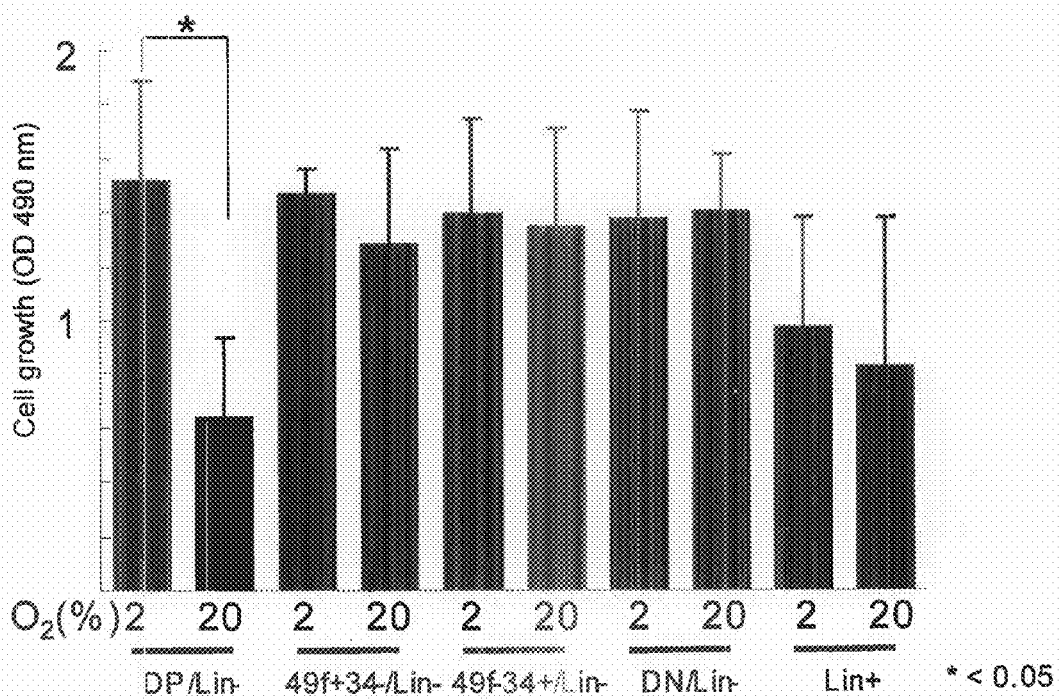

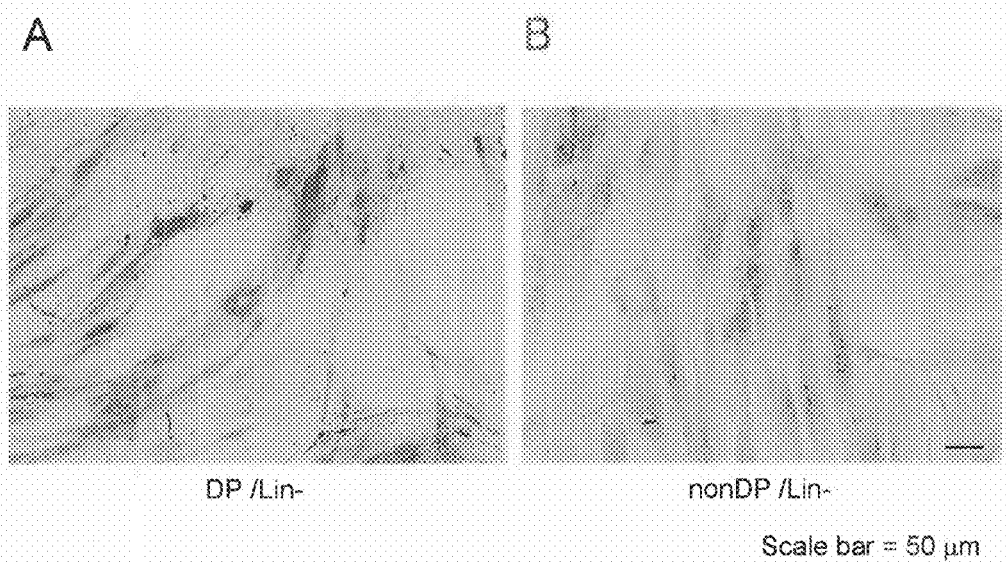

Fig. 4
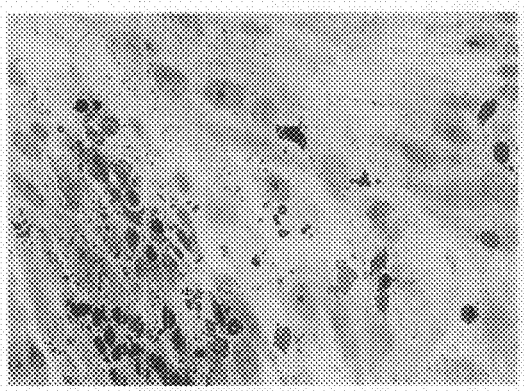
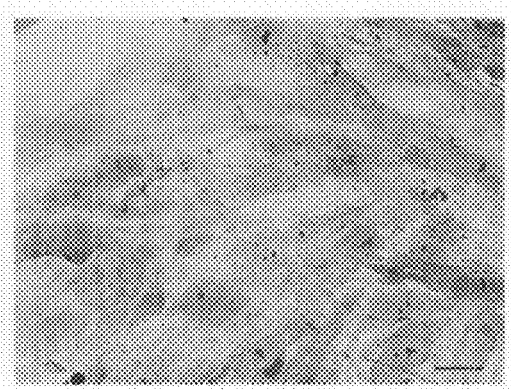
A — DP /Lin-
B — nonDP /Lin-
Scale bar = 30 μm

Fig. 5
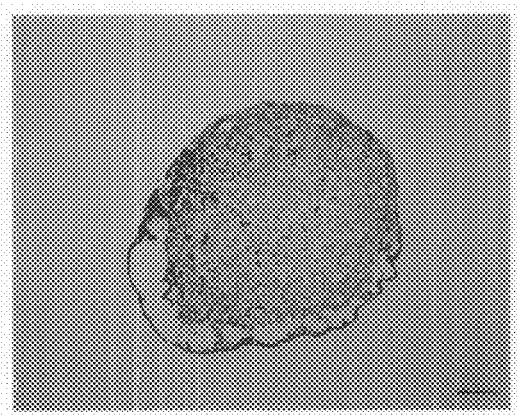
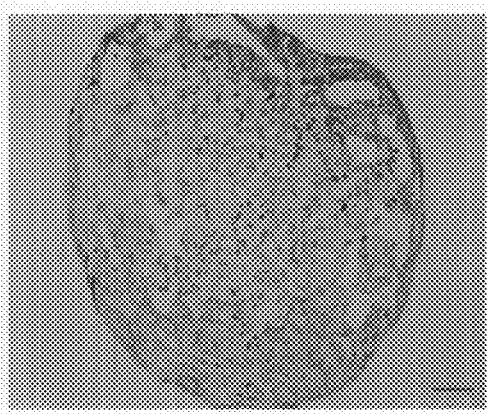
A  
Scale bar = 100 μm
B  
Scale bar = 50 μm

E2 pellet (+)

Fig. 9
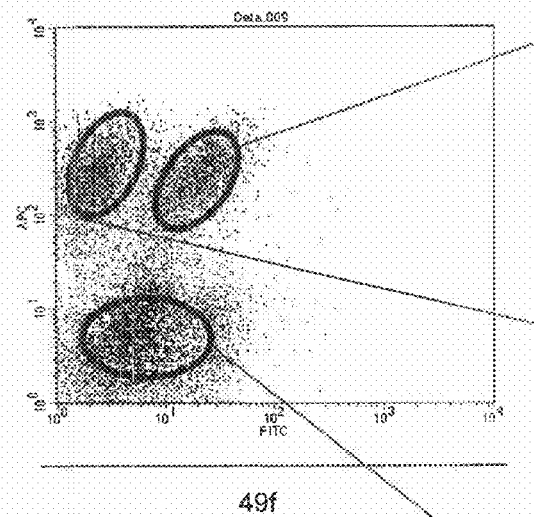
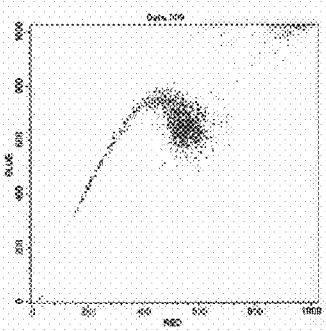
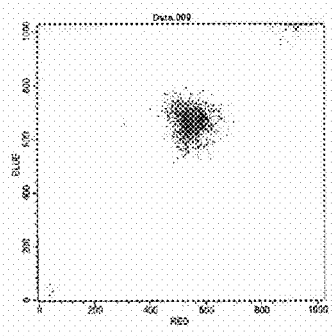
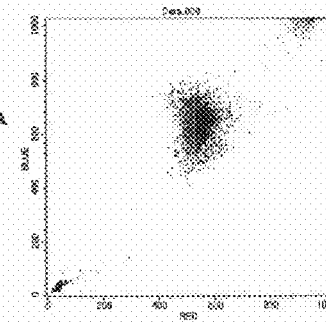

A: after 1 d
B: after 7 d
C: after 14 d
D: after 21 d

E and F: a colony continued to grow

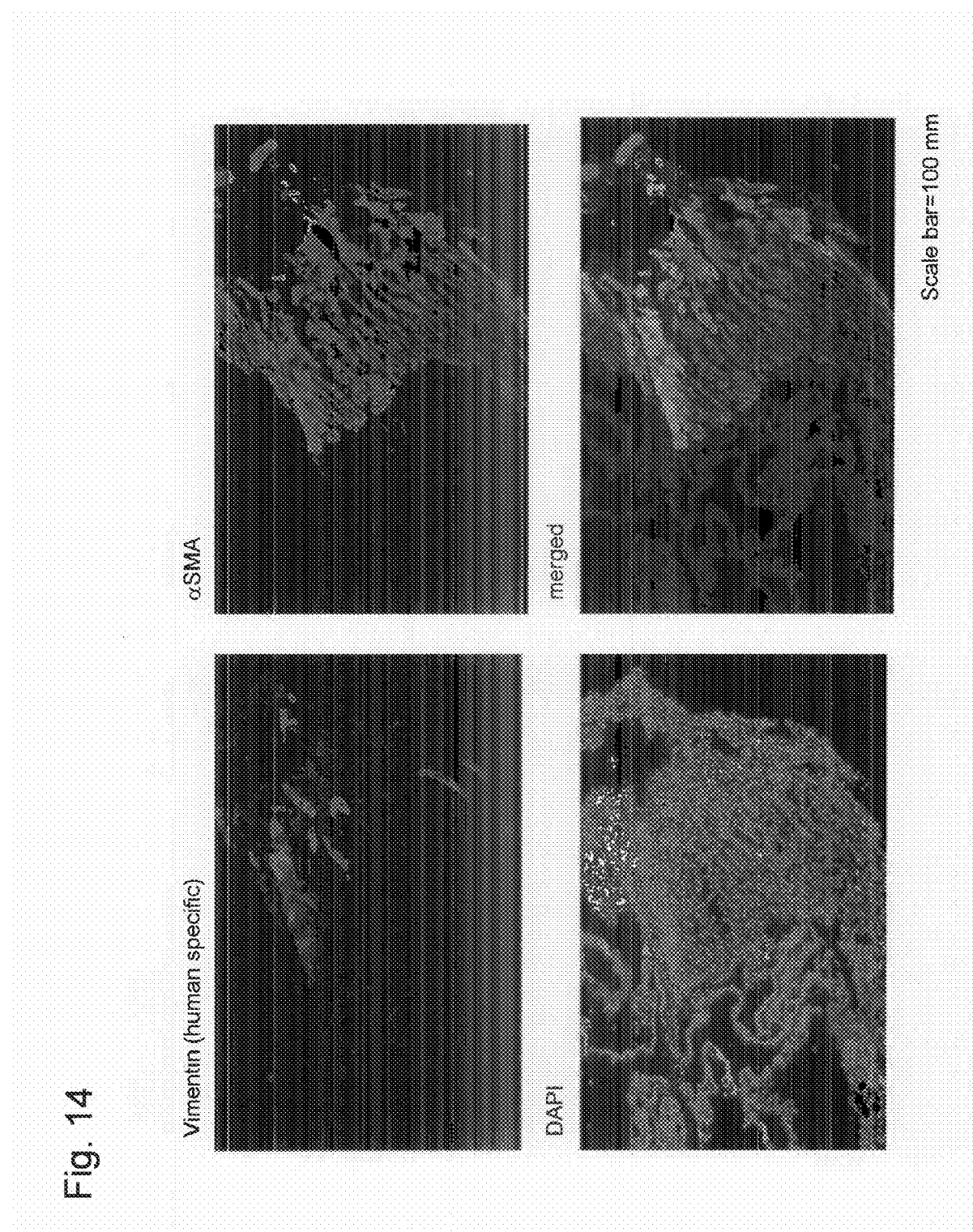

METHOD FOR ISOLATING SMOOTH MUSCLE STEM CELLS

This application is a National Stage of PCT/JP09/057,809 filed Apr. 13, 2009 and claims the benefit of JP 2008-103867 filed Apr. 11, 2008.

TECHNICAL FIELD

The present invention relates to smooth muscle-derived tissue stem cells having a given surface marker, a novel method for isolating the same, a novel method for culturing the same, and applications thereof.

BACKGROUND ART

Recently, stem cells of organisms (tissues) specific to a variety of organs or tissues have been found to play significant roles in maintenance and regeneration of the relevant organs or tissues. Up to the present, stem cells derived from a variety of tissues have been reported and isolated.

Examples of stem cells isolated to date include skeletal muscle stem cells, cardiac muscle stem cells, liver stem cells, neural stem cells, pancreatic stem cells, epidermal stem cells, and adipose tissue stem cells. Stem cells are often isolated by the side population (SP) method, and the present inventors previously isolated the smooth muscle stem cells from the human uterus by the SP method (see JP Patent Publication (kokai) No. 2007-202435 A).

At present, regenerative medicine has drawn a great deal of attention as a form of medical treatment for restoring cells or tissues of human bodies that have been damaged or lost due to diseases or injuries and recovering the functions thereof. If the above tissue stem cells could be isolated, identified, replicated and multiplied, it would be possible to achieve regenerative medical treatments.

SUMMARY OF THE INVENTION

The present invention aims to provide smooth muscle stem cells, particularly, uterine muscle stem cells, and the application of such stem cells.

A type of smooth muscle (i.e., the uterine muscle) can undergo a significant increase in cell size (i.e., hypertrophy) and an increase in the number of cells (i.e., hyperplasia) because of pregnancy year by year, and such dramatic changes can be repeated 20 or more times throughout a woman's life. The uterine muscle is a very unique tissue, and it is known to undergo significant hypertrophy and hyperplasia upon pregnancy and childbearing and to rapidly undergo apoptosis during the puerperal period.

The inventors focused on a series of events from an increase in the number of cells to apoptosis during the period of pregnancy to puerperium and considered the possibility that tissue stem cells could be present in the uterine smooth muscle, which is a major constitutive tissue of the uterine muscle. The inventors previously invented a method for isolating smooth muscle stem cells from the human uterus using the SP method (see JP Patent Publication (kokai) No. 2007-202435 A). The SP method, however, which involves a step of selection via application of UV lasers following a reaction with a DNA dye, imposes damages on cells and cannot secure safety and sterility of the isolated stem cells.

Therefore the inventors attempted to isolate stem cells with the use of surface markers as a method that would impose little damage on cells and secure safety or sterility of isolated cells. Specifically, the inventors sampled normal uterine muscle layer, obtained dispersed cells via an enzyme treatment, selected Lin (CD31, CD45, and Glycophorin A)-negative cells via flow cytometry, and sorted such Lin-negative cells into CD34-positive/CD49f-positive cells (i.e., double-positive cells; DP/Lin–) and other cells (nonDP). At last, the inventors isolated double-positive cells (DP/Lin–), which are CD31-, CD45-, and Glycophorin A-negative and CD34- and CD49f-positive, from the dispersed cells via FACS as uterine muscle DP/Lin– cells.

The inventors discovered that the double-positive cells (DP), which are CD34- and CD49f-positive, could be isolated as uterine muscle DP cells based only on CD34 and CD49f expression. In this case, the inventors also discovered that the double-positive (DP) cells could be isolated as uterine muscle DP cells that are CD34- and CD49f-positive from among CD45-negative cells that had been selected in advance.

Subsequently, the inventors analyzed the genes expressed in the DP/Lin– cells, the DP cells, and uterine muscle cells other than the DP/Lin– cells and confirmed that the gene expressions in the DP/Lin– and DP cells showed the features of stem cells. Further, the inventors discovered that DP/Lin– and DP could be differentiated into bone, fat, and cartilage cells in vitro and transplantation of DP/Lin– and DP into immunodeficient mice enabled to reconstruct uterine muscle-like tissue. The inventors then confirmed that the isolated cells were uterine smooth muscle stem cells.

Thus, the present invention is as follows.

[1] A method for isolating smooth muscle stem cells derived from mammalian smooth muscle, which comprises bringing the mammalian smooth muscle cells into contact with an anti-CD31 antibody, an anti-CD45 antibody, an anti-Glycophorin A antibody, an anti-CD34 antibody, and an anti-CD49f antibody labeled with fluorescent dyes and isolating cells that do not bind to the anti-CD31 antibody, the anti-CD45 antibody, and the anti-Glycophorin A antibody but bind to the anti-CD34 antibody and the anti-CD49f antibody.

[2] A method for isolating smooth muscle stem cells derived from mammalian smooth muscle, which comprises bringing the mammalian smooth muscle cells into contact with an anti-CD34 antibody and an anti-CD49f antibody labeled with fluorescent dyes and isolating cells that bind to the anti-CD34 antibody and the anti-CD49f antibody.

[3] The method for isolating smooth muscle stem cells derived from the mammalian smooth muscle according to [2], which comprises bringing the mammalian smooth muscle cells into contact with an anti-CD45 antibody, an anti-CD34 antibody, and an anti-CD49f antibody labeled with fluorescent dyes and isolating cells that do not bind to the anti-CD45 antibody but bind to the anti-CD34 antibody and the anti-CD49f antibody.

[4] The method for isolating smooth muscle stem cells according to any of [1] to [3] comprising sorting cells via flow cytometry.

[5] The method for isolating smooth muscle stem cells according to [1] comprising sorting the mammalian smooth muscle cells into Lin (CD31, CD45, and Glycophorin A)-positive cells (Lin+) and Lin-negative cells (Lin–) via flow cytometry, sampling the Lin-negative cells, and further sampling the CD34-positive and CD49f-positive cells.

[6] The method for isolating smooth muscle stem cells according to [2] comprising sampling the CD34-positive and CD49f-positive cells from mammalian smooth muscle cells via flow cytometry.

[7] The method for isolating smooth muscle stem cells according to [3] comprising sampling the CD45 negative cells from mammalian smooth muscle cells via flow cytometry and further sampling the CD34-positive and CD49f-positive cells.

[8] The method for isolating smooth muscle stem cells according to any of [1] to [7], wherein the smooth muscle is uterine muscle.

[9] The method for isolating smooth muscle stem cells according to any of [1] to [8], wherein the mammalian is a human.

[10] Smooth muscle stem cells isolated by the method according to any of [1] to [9], which are CD31-, CD45-, and Glycophorin A-negative and CD34- and CD49f-positive.

[11] Smooth muscle stem cells isolated by the method according to any of [1] to [9], which are CD34- and CD49f-positive.

[12] Smooth muscle stem cells isolated by the method according to any of [1] to [9], which are CD45-negative and CD34- and CD49f-positive.

[13] The smooth muscle stem cells according to any of [10] to [12], which are further ABCG2-positive.

[14] The smooth muscle stem cells according to any of [10] to [13], which are capable of being differentiated into smooth muscle upon transplantation thereof to smooth muscle.

[15] The smooth muscle stem cells according to [14] derived from uterine muscle, which are capable of being differentiated into uterine muscle upon transplantation thereof into uterine muscle.

[16] A composition for regenerating the smooth muscle tissue comprising the smooth muscle stem cells according to any of [10] to [15].

This description includes part or all of the contents as disclosed in the description and/or drawings of Japanese Patent Application No. 2008-103867, which is a priority document of the present application.

BRIEF DESCRIPTION OF THE DRAWINGS

FIG. 1-1 shows the results of flow cytometry analysis of uterine muscle dispersed cells stained with a fluorescence-labeled antibody. FIG. 1-1A shows the cell distribution of the Lin (CD31, CD45, and Glycophorin A) positive cells (Lin+) separated from the negative cells (Lin-). FIG. 1-1 B shows the cell separation of the Lin (CD31, CD45, and Glycophorin A) positive cells (Lin+) (Lin+ fraction) from the Lin negative cells (Lin-) (Lin- fraction). FIG. 1-1 C shows the distribution of CD34-positive/CD49f-positive cells (double-positive cells (DP/Lin-)) of Lin- cells (Lin- fraction).

FIG. 1-2 shows the results of expression analysis of ABCG2 in DP/Lin-, nonDP/Lin-, and Lin+ via RT-PCR. In the figure, "Tissue" indicates uterine muscle cells when dispersed via mechanical or enzymatic treatment (i.e., DP/Lin-, nonDP/Lin-, and Lin+), and "NC" indicates a negative control using a distilled water template.

FIG. 2 shows a chart showing the growth of DP/Lin- cultured at a normal oxygen concentration of 20% or a low oxygen concentration of 2% and other fractions using cell growth activity as the indicator.

FIG. 3 shows microscopic images of DP/Lin- (FIG. 3A) and nonDP/Lin- (FIG. 3B) cultured in a bone cell-inducing medium stained with alkaline phosphatase.

FIG. 4 shows microscopic images of DP/Lin- (FIG. 4A) and nonDP/Lin- (FIG. 4B) cultured in a fat cell-inducing medium stained with oil red O.

FIG. 5 shows a microscopic image of DP/Lin- cultured in a cartilage cell-inducing medium stained with toluidine blue. Scale between FIG. 5A and FIG. 5B is different.

FIG. 6A shows a photograph of a fluorescent immunostaining image stained for human vimentin and TOTO-3 (nuclear stain) and further stained for α-smooth muscle action (αSMA) (A), OTR (oxytocin receptor) (B) or HNA (human nucleic antigen).

FIG. 9 shows the results of flow cytometry analysis of uterine muscle dispersed cells that have not undergone pre-selection with the use of the Lin marker stained with the fluorescence-labeled antibody. FIG. 9A shows cell distribution for the entire cell population and FIGS. 9B, 9C, and 9D show cell distribution for the DP (double-positive; CD49f(+)CD34(+)) fraction, the CD49f(-)CD34(+) fraction, and the CD34(-) fraction, respectively.

FIG. 10A shows cell distribution for the entire cell population and FIG. 10B shows cell distribution for the DP fractions. FIG. 10C shows CD31 expression patterns for the DP fractions, FIG. 10D shows cell distribution for the CD31(+) fractions, and FIG. 10E shows cell distribution for the CD31(-) fractions.

FIGS. 12A, 12B, 12C and 12D show the colony formation on day 1, day 7, day 14 and day 21, respectively FIGS. 12E and 12F show the conditions of growing colonies.

FIG. 14 shows a fluorescent immunostaining image of the uterus of a immunodeficient mouse into which DP fraction had been transplanted. FIG. 14 upper left panel shows the result of vimentin (human specific) staining. FIG. 14 upper right panel shows the result of αSMA staining, FIG. 14 left below panel shows the result of DAPI staining (nuclear staining). FIG. 14 right below panel shows the result of merged image of vimentin staining, αSMA staining and DAPI staining.

BEST MODES FOR CARRYING OUT THE INVENTION

Figures 1, 2:
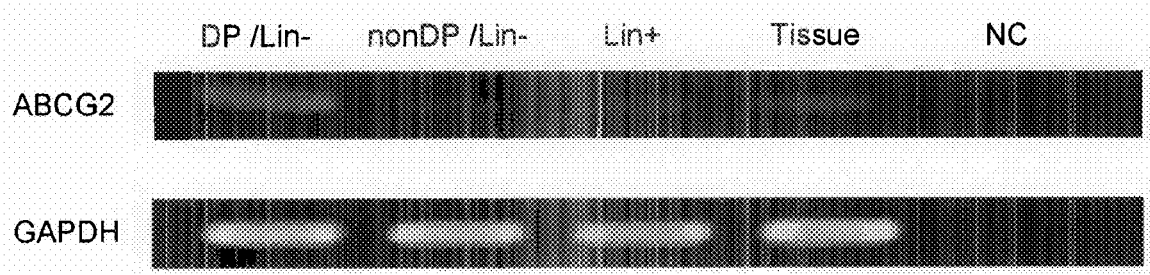

The stem cells of the present invention are smooth muscle-derived tissue stem cells isolated from smooth muscle. Examples of smooth muscle from which the stem cells of the present invention are derived include uterine smooth muscle, visceral smooth muscle, and vascular smooth muscle, with uterine smooth muscle being preferable. Tissue sections thereof are sampled, cells are dispersed, and stem cells can be isolated from the dispersed cells. For example, fibroid slices can be used. Smooth muscle can be sampled from any animal species, and examples thereof include mammalians, such as mice, rats, guinea pigs, hamsters, rabbits, cats, dogs, sheep, pigs, cows, horses, goats, monkeys, and humans.

The term "stem cells" used herein refers to cells that can selfrenew and are multipotent. In general, stem cells are capable of regenerating tissues when such tissues are damaged. Unlike embryonic stem cells, the differentiation directions of tissue stem cells are limited, tissue stem cells are located in given positions of the tissue, and they have undifferentiated intracellular structures. Accordingly, tissue stem cells have limited multipotency. Tissue stem cells have a high nuclear-cytoplasmic ratio and a small number of cell organella. In general, tissue stem cells are multipotent, they demonstrate a slow cell cycle, and they retain growth ability for a period longer than the life of an individual. In the present invention, the term "stem cells" refers to a cell population including a given amount or more of stem cells, such as a cell population in which stem cells account for 90% or more, and preferably 95% or more, of the cells.

The smooth muscle stem cells of the present invention are Lin− cells, which are CD34-positive and CD49f-positive. The term "Lin− cells" refers to differentiation antigen-negative cells, which do not have surface antigens that express with differentiation of stem cells into cells of a given lineage (i.e., cells on the surfaces of which such surface antigens are not expressed). In the present invention, Lin− cells are CD31-, CD45-, and Glycophorin A (GPA)-negative cells. CD31 antigens are expressed in almost all monocytes, platelets, and granulocytes, CD45 antigens are expressed in all leucocytes including peripheral blood lymphocytes, monocytes, granulocytes, acidocytes, and basocytes, and GPA antigens are associated with erythrocytes. CD34 cells are expressed in stem cells which are undifferentiated, and CD49f cells are expressed in platelets or blood megakaryocytes. In the present invention, CD34-positive and CD49f-positive cells are referred to as "double-positive (DP) cells," and Lin−, CD34-positive, and CD49f-positive cells are referred to as "DP/Lin− cells." In the smooth muscle stem cells of the present invention, further, the ABCG2 stem cell marker is expressed (ABCG2: ATP-binding cassette transporter G2).

In addition, the smooth muscle stem cells of the present invention are CD34-positive and CD49f-positive cells. Such cells may be CD45-, CD31-, and Glycophorin A-negative or positive. In the present invention, such cells are also referred to as double-positive (DP) cells.

The stem cells of the present invention can be isolated based on antigen properties on the surfaces of smooth muscle cells. Specifically, Lin− cells, which are CD34-positive and CD49f-positive, may be isolated from smooth muscle cells.

Alternatively, the stem cells of the present invention may be obtained by isolating CD34-positive and CD49f-positive cells from smooth muscle cells based only on the expression of CD34 and CD49f. In such a case, CD45-negative cells may be selected in advance, and CD34-positive and CD49f-positive cells may be isolated therefrom.

First, cells are dispersed from smooth muscle. Cells can be dispersed by slicing tissue sections and treating the sliced tissue sections with an enzyme such as collagenase. The dispersed cells are preferably dispersed to be in a state of single cells. For example, the dispersed cells are applied to a cell strainer, the resultant is subjected to density gradient centrifugation with the use of a specific gravity solution such as Ficoll-Paque®, and the product is treated with trypsin, so that the cells can be dispersed as single cells.

Subsequently, antibodies reacting with CD31, CD45, Glycophorin A, CD34, and CD49f or ABCG2 each labeled with a different fluorescent dye are brought into contact with the dispersed smooth muscle cells to stain smooth muscle cells having surface antigens, and DP/Lin− cells are sorted via flow cytometry or FACS. Thus, the smooth muscle stem cells of the present invention can be isolated. In such a case, the cells of interest may be directly isolated from the smooth muscle cells via flow cytometry, or cells having differentiation antigens are removed with the use of magnetic beads to which an antibody reacting with at least 1 type of antigen selected from among CD31, CD45, and Glycophorin A has been bound before sorting via flow cytometry, and the cells of the present invention may be isolated via FACS from the remaining cells.

Also, antibodies reacting with CD34 and CD49f or CD45, CD34, and CD49f each labeled with a different fluorescent dye are brought into contact with the dispersed smooth muscle cells to stain smooth muscle cells having surface antigens, and DP cells are sorted via flow cytometry or FACS. Thus, the smooth muscle stem cells of the present invention can be isolated. In such a case, CD34- and CD49f-positive cells may be directly isolated from the smooth muscle cells via flow cytometry. Alternatively, cells containing CD45 are removed with the use of magnetic beads to which antibodies reacting with CD45 are bound prior to sorting via flow cytometry, and the cells of the present invention may be isolated from the remaining cells via FACS.

Examples of fluorescent dyes used for labeling include Cy™ 3, Cy5, Texas Red®, APC (allophycocyanin), PE (phycoerythrin), PE-Cy5, FITC (fluorescein isothiocyanate), and PerCP. The FACS vantage (manufactured by Becton, Dickinson and Company), the FACS Calibur (manufactured by Becton, Dickinson and Company), or the like can be used for flow cytometry or FACS.

The isolated stem cells of the present invention can be multiplied by culture. In this case, a medium to be used is not limited, and a known medium such as DMEM (Dulbecco's modified Eagle's medium) can be used. Use of known medium for stem cell culture is particularly preferable. For example, a mesenchymal stem cell basal medium (MSCBM) (former name: Cambrex Bio Science; current name: Poietics) or a mesenchymal stem cell growth medium (MSCGM) (former name: Cambrex Bio Science; current name: Poietics) can be used. Blood serum, such as fetal bovine serum, antibiotics, such as penicillin or streptomycin, and a variety of physiologically active substances may be added to a medium, according to need. The stem cells of the present invention are cultured at an oxygen concentration lower than the normal level of 20%. The oxygen concentration is preferably 5% or lower, more preferably 2.5% or lower, and particularly preferably 2%. Thus, stem cells can be multiplied. Cells may be sowed and cultured on a culture dish for tissue culture.

Furthermore, the isolated stem cells of the present invention can differentiate into given tissue cells in vitro. Since the stem cells of the present invention are multipotent, such cells can be basically induced into arbitrary tissue cells. Differentiation-inducing media for a variety of tissues are commercialized, and cell differentiation can be induced with the use of such commercially available media. When stem cells are induced to differentiate into bone cells, for example, the BulletKit osteoblast differentiation medium (former name: Cambrex Bio Science; current name: Poietics) may be used. When stem cells are induced to differentiate into fat cells, the BulletKit fat cell differentiation medium (former name: Cambrex Bio Science; current name: Poietics) may be used. When stem cells are induced to differentiate into cartilage cells, the BulletKit cartilage cell differentiation medium (Cambrex Bio Science) may be used. Also, the smooth muscle stem cells of the present invention can be induced to differentiate into smooth muscle tissue cells, such as the uterine muscle tissue cells. In such a case, culture is conducted at an oxygen concentration that is employed for common cell culture (i.e., about 20%). The cells differentiated into such tissue cells may further be cultured to construct tissues.

Whether or not stem cells have been induced to differentiate into tissue cells can be determined by inspecting the expression of markers specific to relevant tissue cells. For example, differentiation into bone cells can be inspected based on the presence or absence of cells stained positive with alkaline phosphatase, and differentiation into fat cells may be inspected based on the presence or absence of cells stained positive with oil red O. Further, differentiation into cartilage cells can be inspected based on the presence or absence of cartilage pellets stained positive with toluidine blue.

In addition, the present invention includes established cell lines prepared by immortalizing the smooth muscle stem cells of the present invention. Such established cell lines have the ability to proliferate and multipotency, and such cells may be allowed to proliferate to the necessary number and then used. The established cell lines can be utilized as instruments for the study of differentiation and generation of smooth muscle. Human cells are converted into immortal cells (occasionally cancer cells) because of radioactive rays, mutagens, or viruses. In recent years, in particular, human telomerase reverse transcriptase genes (hTERTs), SV40T genes, or the like are introduced into cells as a method for immortalizing cells without causing tumorigenesis or chromosome anomaly while maintaining original cell properties to a relatively significant extent.

The smooth muscle stem cells of the present invention can be used for regenerative medicine or other applications. For example, the smooth muscle stem cells of the present invention may be administered to damaged smooth muscle via injection with the use of a syringe, so that stem cells are differentiated into smooth muscle cells, and the damaged smooth muscle can be reconstructed. Also, the stem cells of the present invention may be induced to differentiate in vitro as described above to construct tissue, and the resulting tissue may be transplanted. In order to avoid rejection of the transplanted cells or tissue by a recipient in cases of such regenerative medicine, it is preferable that tissue sections are sampled from a patient who will receive regenerative medicine and the smooth muscle stem cells of the present invention are isolated from such tissue sections and used. For example, tissue sections are sampled from the remaining uterine muscle of a patient who has undergone a partial hysterectomy because of a disease such as uterine sarcoma, uterine muscle stem cells are isolated from the tissue sections, and the isolated stem cells can be used for reconstruction of the uterus of the patient. As described above, the smooth muscle stem cells of the present invention can be differentiated into other tissues. For example, tissue sections are sampled from smooth muscle such as uterine muscle of a patient who had suffered from injury of a given tissue other than smooth muscle, smooth muscle stem cells are isolated, and such cells are induced to differentiate into tissue of the damaged smooth muscle stem cells. Thus, the resultant can be used for regenerative medicine of tissue other than smooth muscle. The present invention also includes a composition used for regenerative medicine comprising the stem cells of the present invention (i.e., a pharmaceutical composition for regenerative medicine).

Further, the human-derived stem cells of the present invention may be transplanted into immunodeficient animals other than humans, so that animal models that are partially composed of human smooth muscle tissue can be obtained. For example, the smooth muscle stem cells of the present invention may be transplanted into the smooth muscle of an immunodeficient animal, so that the stem cells of the present invention are differentiated into smooth muscle, and human smooth muscle tissue is constructed in part of an animal body. Whether or not the human smooth muscle tissue is constructed in an animal body may be determined by assaying proteins specific to the human smooth muscle expressed in the cells and inspecting whether or not the constructed smooth muscle cells have morphological features of smooth muscle. In the case of uterine smooth muscle, for example, whether or not the uterine smooth muscle is vimentin-positive (i.e., the uterine smooth muscle is derived from a human (red) and is αSMA positive (green)), and whether or not the uterine smooth muscle has morphological features of uterine smooth muscle may be inspected. The thus-obtained animal partially composed of human smooth muscle tissue can be used as an animal model having human smooth muscle tissue. When the smooth muscle is uterine muscle, for example, such smooth muscle can be used for screening for a drug that cause the uterus to contract or relax. When the smooth muscle stem cells of the present invention are subjected to canceration and transplanted, also, animal models having human uterine cancer or the like can be prepared, and such animal models can be used for screening for a therapeutic agent. Examples of immunodeficient animals include immunodeficient mice, such as said mice and NOG mice.

The present invention is described in detail with reference to the following examples, although the present invention is not limited thereto.

Example 1

Preparation of Double-Positive Uterine Muscle Cells
(DP/Lin-Cells)

(1) Preparation of Monodispersed Uterine Muscle Cells

Fibroid slices isolated from the human uterus were further sliced to pieces of about 2 mm$^3$ with the use of scissors, the resulting pieces were introduced into a DMEM medium (Dulbecco's Modified Eagle's Medium (DMEM: Sigma-Aldrich, Missouri, U.S.A.) containing 1% antibiotics-antimycotic agent (GIBCO) and 10% fetal bovine serum (BioWest, Florida, U.S.A.)) containing 0.2% (w/v) collagenase (Wako Pure Chemical Industries, Ltd., Osaka, Japan) and 0.05% (w/v) DNaseI (GIBCO, California, U.S.A.) in amounts of 1 g of the tissue sections per 10 ml of medium, and cells were enzymatically dispersed via agitation at 37° C. for 16 hours. Subsequently, the resultant was filtered through a polyethylene mesh (pore diameter: 400 μm), and the cells were allowed to pass through a cell strainer (pore diameter: 40 μm, BD Biosciences, Massachusetts, U.S.A.) to disperse the cells to result in a state of single cells. Subsequently, the dispersed cells were superposed on the Ficoll-Paque PLUS (Amersham Biosciences, New Jersey, U.S.A.), density gradient centrifugation was carried out at 780×g for 15 minutes, and a dispersion of single cells was recovered from the interface layer. The dispersion was subjected to enzyme treatment with the use of a 0.05% (w/v) trypsin-EDTA (Sigma-Aldrich)·0.05% (w/v) DNaseI solution and pipetting to prepare a population of completely dispersed cells.

(2) Staining of Cells with Fluorescence-Labeled Antibody

The above population of dispersed single uterine muscle cells was suspended in Hanks' balanced salt solution (free of calcium and magnesium, HBSS$^+$) containing 2% fetal calf serum, 10 mM HEPES, and 1% penicillin and streptomycin at a concentration of 2×10$^6$, and the reaction was allowed to proceed at 4° C. for 30 minutes with the addition of fluorescence-labeled antibodies. Subsequently, the resultant was centrifuged at 4° C., suspended in 2 ml of Hanks' balanced salt solution, and stained with propidium iodide (PI) in order to select dead cells.

The fluorescence-labeled antibodies used were the PE-bound anti-CD31 antibody (IgG1, BD Biosciences), the PE-bound anti-CD45 antibody (IgG1, BD Biosciences), the PE-bound anti-Glycohporin A antibody (IgG2b, BD Biosciences), the APC-bound anti-CD34 antibody (IgG1, BD Biosciences), and the FITC-bound anti-CD49f antibody (IgG2a, BD Biosciences).

(3) Separation of Double-Positive Uterine Muscle Cells (DP/Lin−)

The cell population was two-dimensionally developed via flow cytometry based on fluorescence intensities. The stained dispersed cells were analyzed via flow cytometry (FACS Vantage SE, Becton Dickinson) and using analytical software (Cell-Quest, Becton Dickinson).

FIG. 1 shows the cell distribution. Thus, $1 \times 10^5$ cells were collected with two-dimensional development, the Lin (CD31, CD45, and Glycophorin A) positive cells (Lin+) were separated from the negative cells (Lin−) (FIGS. 1-1A and 1-1B), and CD34-positive/CD49f-positive cells (double-positive cells (DP/Lin−)) were separated from other cells (nonDP/Lin−) (FIG. 1-1C). The double-positive cells were fractionated in the end (the DP/Lin− fraction) and designated as uterine muscle DP/Lin− cells.

(4) Analysis of Differentiation Marker Gene Expression

Total RNA was extracted from the separated DP/Lin−, nonDP/Lin−, and Lin+ cells using Trizol (Invitrogen, California, U.S.A.), and expression of ABCG2 messenger RNA was analyzed via the reverse-transcriptase polymerase chain reaction (RT-PCR). FIG. 1-2 shows the results thereof. There was no difference in the GAPDH expression level (i.e., the internal standard) therebetween. This indicates that the ABCG2 stem cell marker is expressed in the DP/Lin− cells at a higher level than in other fractions, the degree of differentiation is lower (i.e., immature), and DP/Lin− cells have properties equivalent to those of tissue stem cells.

Example 2

Culture of Double-Positive Uterine Muscle Cells (DP/Lin− Cells)

Culture was conducted in the Multi-Gas Incubator (Astec Co., Ltd., Fukuoka, Japan) at a low oxygen concentration of 2% instead of a general oxygen concentration for culture (i.e., 20%).

As a result, cells proliferated poorly 3 weeks later when cultured at an oxygen concentration of 20%; however, cell colonies were formed 1 week after the initiation of culture at a low oxygen concentration of 2%, and cells were grown to reach confluence 2 weeks later (FIG. 2).

Example 3

Assay of Induced Differentiation of Double-Positive Uterine Muscle Cells (DP/Lin− Cells)

In order to inspect whether or not the above cultured DP/Lin− cells have multipotency, which is a feature of stem cells, DP/Lin− cells were cultured in media capable of inducing cells to differentiate into fat cells, bone cells, or cartilage cells to inspect if such cells could be differentiated into cells of different lineages.

As a medium to induce cells to differentiate into bone cells, the Prekit osteoblast differentiation medium (manufactured by Cambrex Bio Science, sold by Sanko Junyaku Co., Ltd., Product Number PT-3002) was used. As a medium to induce cells to differentiate into fat cells, the Prekit fat cell differentiation medium (manufactured by Cambrex Bio Science, sold by Sanko Junyaku Co., Ltd., Product Number PT-3004) was used. As a medium to induce cells to differentiate into cartilage cells, the Prekit cartilage cell differentiation medium (manufactured by Cambrex Bio Science, sold by Sanko Junyaku Co., Ltd., Product Number PT-4121) was used. The cultured DP/Lin− cells and DP/Lin nonDP/Lin− cells were sowed on a 96-well plate at a density of about $5 \times 10^3$/well, and culture was conducted until confluence in an MSCGM medium at an oxygen concentration of 2% (i.e., a low oxygen concentration) for about 2 to 3 weeks. When the culture for differentiation induction described below was initiated, the oxygen concentration was returned to a general level of 20%, and cells were induced to differentiate.

Differentiation into Bone Cells

The cultured DP/Lin− cells were induced to differentiate into bone cells. The bone-cell-inducing medium was exchanged every 3 or 4 days, and culture was continued for 2 to 3 weeks. Cell differentiation into bone cells was evaluated based on the appearance of cells stained positive with alkaline phosphatase. As a result, many DP/Lin− cells were found to be stained positive with alkaline phosphatase (purple) (FIG. 3A); however, substantially no non DP/Lin− cells were stained positive therewith (FIG. 3B).

Differentiation into Fat Cells

The cultured DP/Lin− cells were induced to differentiate into fat cells. At the outset, the cells were cultured in the above basal medium for fat cell culture for 3 days, and the cells were further cultured in a medium that induces cells to differentiate into fat cells for 1 to 3 days. This cycle was repeated 3 times, and culture was continued in a basal medium for 1 week at maximum in the end. Thereafter, the cells were washed, fixed, and stained with oil red O in order to stain fat drops. As a result, DP/Lin− cells that were stained positive with oil red O (red) appeared (FIG. 4A); however, substantially no nonDP/Lin− cells were stained positive therewith (FIG. 4B).

Differentiation into Cartilage Cells

The cultured DP/Lin− cells were induced to differentiate into cartilage cells. The cartilage-cell-inducing medium was exchanged every 3 or 4 days, and culture was three-dimensionally continued in a 15-ml centrifuge tube for 2 to 3 weeks. Cell differentiation into cartilage cells was evaluated based on the appearance of cartilage pellets stained positive with toluidine blue. As a result, DP/Lin-pellets that were stained positive with toluidine blue (purple) appeared (FIG. 5); however, no cartilage pellets of nonDP/Lin− cells were found.

Example 4

Experiment of Double-Positive Uterine Muscle Cell (DP/Lin− Cell) Transplantation into Immunodeficient Mice NOG (NOD/SCID/$\gamma_c^{null}$) mice (the Central Institute for Experimental Animals, Kawasaki, Japan) were anesthetized via intraperitoneal injection of 350 µl of phosphate buffer (Sigma) containing 10% pentobarbital (Dai-Nippon Yakuhin). The roughly $5 \times 10^4$ DP/Lin− and DP/Lin− cells that had been separated were injected into the uterine horns of the NOG mice using a 29 gauge needle and the mice were then raised for 4 to 5 weeks. The NOG mice that had experienced transplantation were divided into three groups 4 to 5 weeks after the transplantation, and kinetic analysis of stem cells in vivo was carried out. First of all, two tablets of estrogen ($E_2$)

sustained release pellets (Innovative Research of America, Florida, U.S.A.) were transplanted hypodermically into the first group in order to realize a high estrogen environment. The second group was not subjected to any treatment. At last, the third group was subjected to crossing with male mice and to analysis at 18.5 days of pregnancy.

Fluorescent Staining of Tissue

The uterus was removed, embedded in the Tissue-Tek OCT compound (Sakura Finetech, California, U.S.A.), and sequentially sliced to a thickness of 6 µm with the use of Cryostat (Leica Microsystems, Wetzler, Germany). The resulting frozen slices were fixed in 4% paraformaldehyde at room temperature for 20 minutes and then washed with phosphate buffer. The resultants were subjected to cell membrane permeation treatment with phosphate buffer containing 0.2% Triton X-100 for 10 minutes and then to blocking by being soaked in a 10% bovine serum albumin solution for 30 minutes. Subsequently, these treated slices were allowed to react with antibodies (clone 1A4, 200-fold diluted, DAKO Cytomatio, Denmark) reacting with α-smooth muscle actin (αSMA) (i.e., uterine smooth muscle markers) at 4° C. overnight, and the primary antibodies were detected using Alexa Fluor 488 (for green fluorescence)-labeled secondary antibodies (Molecular Probes, Oregon, U.S.A.) (1000-fold diluted, 37°C., 1 hour). Subsequently, the slices were allowed to react with vimentin antibodies (clone V9), which are directly labeled with a red fluorescent dye (Cy3, Sigma-Aldrich) and selectively react with human cells for fluorescent double staining. Further, the slices were subjected to contrast staining with a nuclear stain (TOTO-3, Molecular Probes). The stained slices were investigated under a TCS SP2 confocal microscope (Leica Microsystems).

Figure 6:
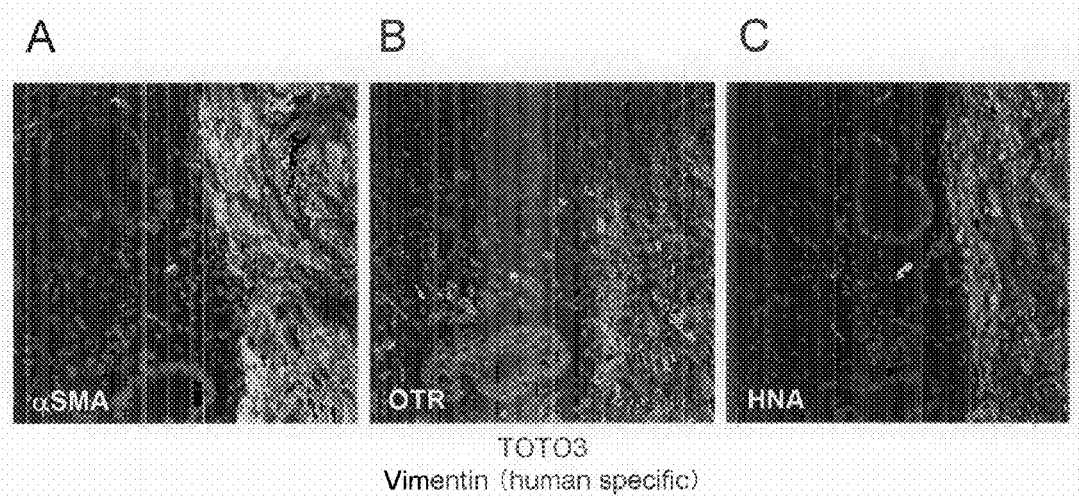
FIG. 6 shows a photograph of a fluorescent immunostaining image of the uterus of a NOG pregnant mouse into which DP/Lin- had been transplanted.
Figure 7:
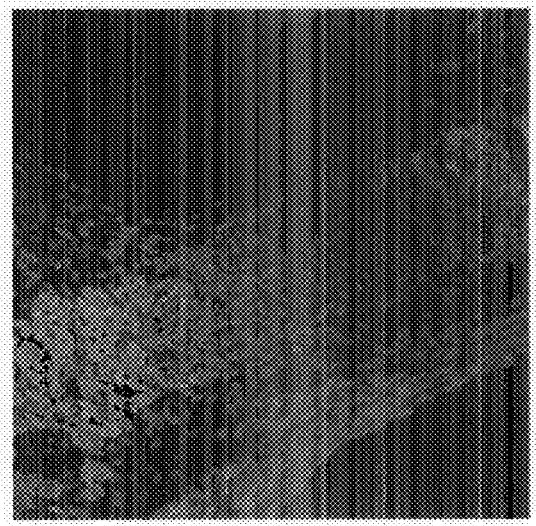
FIG. 7 shows a photograph of a fluorescent immunostaining image of the uterus of a NOG mouse into which an estrogen ($E_2$) sustained release pellet comprising nonDP/Lin- had been transplanted.

As a result, the vimentin-positive tissue; i.e., tissue (yellow) that was derived from a human (red) and αSMA positive (green) and had morphological features of uterine smooth muscle, appeared in the uterus into which DP/Lin− had been transplanted, as shown in FIG. 6. In the uterus into which nonDP/Lin− and Lin+ had been transplanted, however, human derived tissue as observed in the case of DP/Lin− was not observed. Human-derived tissue exists (red) as shown in FIG. 7; however, such tissue is distributed in gaps of the mouse smooth muscle tissue (green).

Figure 8:
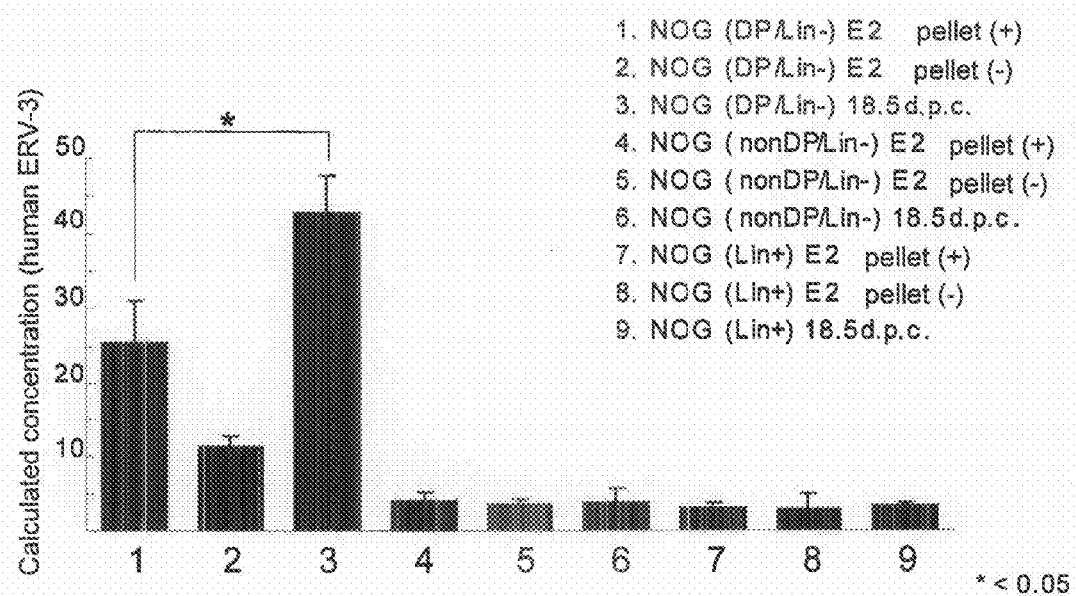
FIG. 8 shows a chart representing the percentage of human cells in the uterus of a NOG mouse into which DP/Lin- or DP/Lin- and Lin+ had been transplanted resulting from the transplantation of an estrogen ($E_2$) sustained release pellet and pregnancy.

Also, DP/Lin− growth is stimulated by estrogen pellets or pregnancy, and the percentage of human-derived cells is found to be elevated quantitatively (FIG. 8).

The above demonstrates that DP/Lin− has the ability to construct the uterine smooth muscle; however, nonDP/Lin− and Lin+ do not have such ability. This indicates that DP/Lin− has specific properties of tissue stem cells of the uterine muscle. Also, DP/Lin− growth was found to be stimulated by estrogen ($E_2$) sustained release pellets or pregnancy.

Example 5

Preparation of Uterine Muscle CD34-Positive/CD49f-Positive Cells (when Preselection with the Use of Lin Marker is not Performed)

Isolated cell fractions were cultured in culture dishes at low cell density of 200 cells/cm$^2$, and colony forming ability was analyzed. At the time of analysis, the cell fractions were scraped off the culture dishes with the use of 20 G needles so as to gain understanding of the behavior of each cultured cell.

(1) Preparation of Monodispersed Uterine Muscle Cells

Fibroid slices isolated from the human uterus were further sliced to pieces of about 2 mm$^3$ with the use of scissors, the resulting pieces were introduced into a DMEM medium (Dulbecco's Modified Eagle's Medium (DMEM: Sigma-Aldrich, Missouri, U.S.A.) containing 1% antibiotics-antimycotic agent (GIBCO) and 10% fetal bovine serum (BioWest, Florida, U.S.A.)) containing 0.2% (w/v) collagenase (Wako Pure Chemical Industries, Ltd., Osaka, Japan) and 0.05% (w/v) DNaseI (GIBCO, California, U.S.A.) in amounts of 1 g of the tissue sections per 10 ml of medium, and cells were enzymatically dispersed via agitation at 37° C. for 16 hours. Subsequently, the resultant was filtered through a polyethylene mesh (pore diameter: 400 µm), and the cells were allowed to pass through a cell strainer (pore diameter: 40 µm, BD Biosciences, Massachusetts, U.S.A.) to disperse the cells to result in a state of single cells. Subsequently, the dispersed cells were superposed on the Ficoll-Paque PLUS (Amersham Biosciences, New Jersey, U.S.A.), density gradient centrifugation was carried out at 780×g for 15 minutes, and a dispersion of single cells was recovered from the interface layer. The dispersion was subjected to an enzyme treatment with the use of a 0.05% (w/v) trypsin-EDTA (Sigma-Aldrich)·0.05% (w/v) DNaseI solution and pipetting to prepare a population of completely dispersed cells.

(2) Staining of Cells with Fluorescence-Labeled Antibody

The above population of dispersed single uterine muscle cells was suspended in Hanks' balanced salt solution (free of calcium and magnesium, HBSS$^+$) containing 2% fetal calf serum, 10 mM HEPES, and 1% penicillin and streptomycin at a concentration of 2×10$^6$, and the reaction was allowed to proceed at 4° C. for 30 minutes with the addition of fluorescence-labeled antibodies. Subsequently, the resultant was centrifuged at 4° C., suspended in 2 ml of Hanks' balanced salt solution, and stained with Propidium Iodide (PI) in order to select dead cells. The fluorescence-labeled antibodies used in Example 1 were used herein.

(3) Separation of Uterine Muscle CD34-Positive/CD49f-Positive Cells

The cell population of PI(−) cells (living cells) and cells that are CD45 negative and have FSC (Forward scatter (forward-scattered light); indicating cell size) of 150 to 500 was two-dimensionally developed via flow cytometry based on fluorescence intensities. The stained dispersed cells were analyzed via flow cytometry (FACS Vantage SE, Becton Dickinson) and using analytical software (Cell-Quest, Becton Dickinson). Differentiation marker gene expression of the fractionated cells was analyzed in the same manner as in Example 1. In addition, the ability to form colony was inspected in the same manner as in Example 2. Further, the fractionated cells were transplanted into severely immunodeficient mice in the same manner as in Example 4.

FIG. 9 shows cell distribution. FIG. 9A shows cell distribution for the entire cell population and FIGS. 9B, 9C, and 9D show cell distribution for the DP (double-positive; CD49f(+)CD34(+)) fraction, the CD49f(−)CD34(+) fraction, and the CD34(−) fraction, respectively. The horizontal axis represents the intensity of CD49f and the vertical axis represents that of CD34. The DP (double-positive) fractions of PI(−) living cells were 9.8%, those of the 49f(−)34(+) fractions were 13.7%, and those of the 34(−) fractions were 43.8%. The DP (CD49f(+)CD34(+)) fractions were fractionated therefrom.

Figure 10:
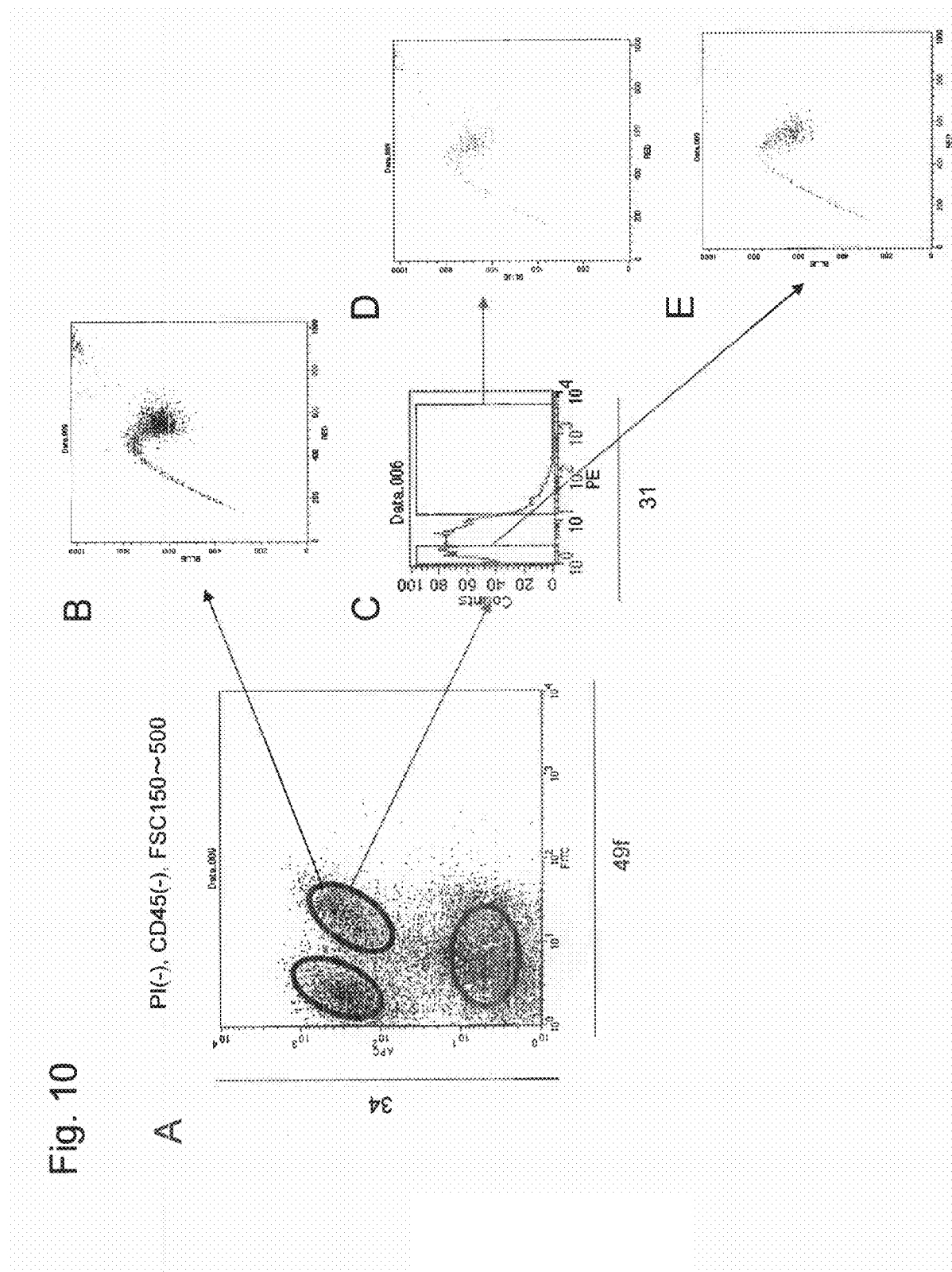
FIG. 10 shows cell distribution of cellular subfractions using CD31 expression in the DP (i.e., double-positive; CD49f(+)CD34(+)) fractions as the indicator.

FIG. 10 shows cell distribution of the cellular subfractions using CD31 expression in the DP fractions as the indicator. As shown in the figure, the DP fractions were further divided into two subfractions (i.e., DP 31+ and DP 31−) based on the occurrence of CD31 expression. FIG. 10A shows cell distribution for the entire cell population and FIG. 10B shows cell distribution for the DP fractions. FIG. 10C shows CD31 expression patterns for the DP fractions, FIG. 10D shows cell distribution for the CD31(+) fractions, and FIG. 10E shows cell distribution for the CD31(−) fractions. The percentage of the PI(−) cells of the population of single uterine muscle accounted for by CD31 positive cells was 3.6% and that accounted for by CD31 negative cells was 3.7%.

Figure 11:
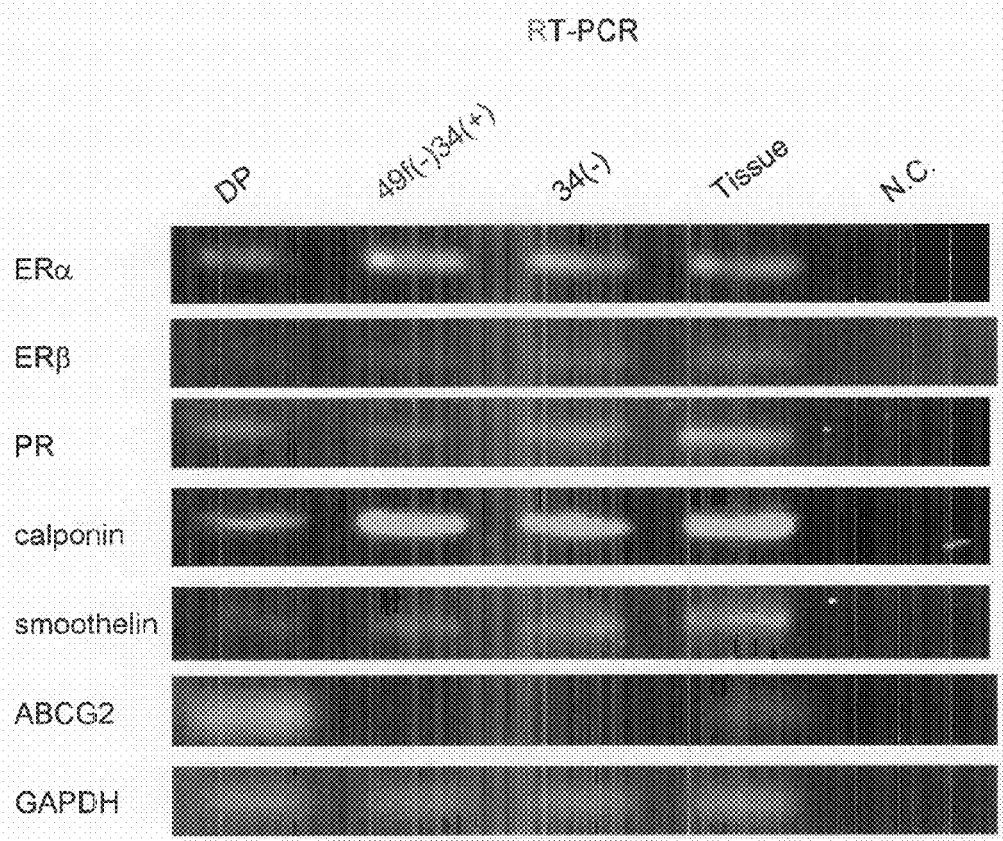
FIG. 11 shows the results of expression analysis of differentiation marker genes in the DP fraction, the CD49f(-)CD34(+) fraction, and the CD34(-) fraction.

FIG. 11 shows the results of expression analysis of differentiation marker genes in the DP fraction, the CD49f(−)CD34 (+) fraction, and the CD34(−) fraction. As shown in FIG. 11, the expression levels of the ERα, ERβ, and smooth muscle differentiation markers of the DP fraction were lower than those of other fractions. In contrast, the ABCG2 expression level was high.

Figure 12:
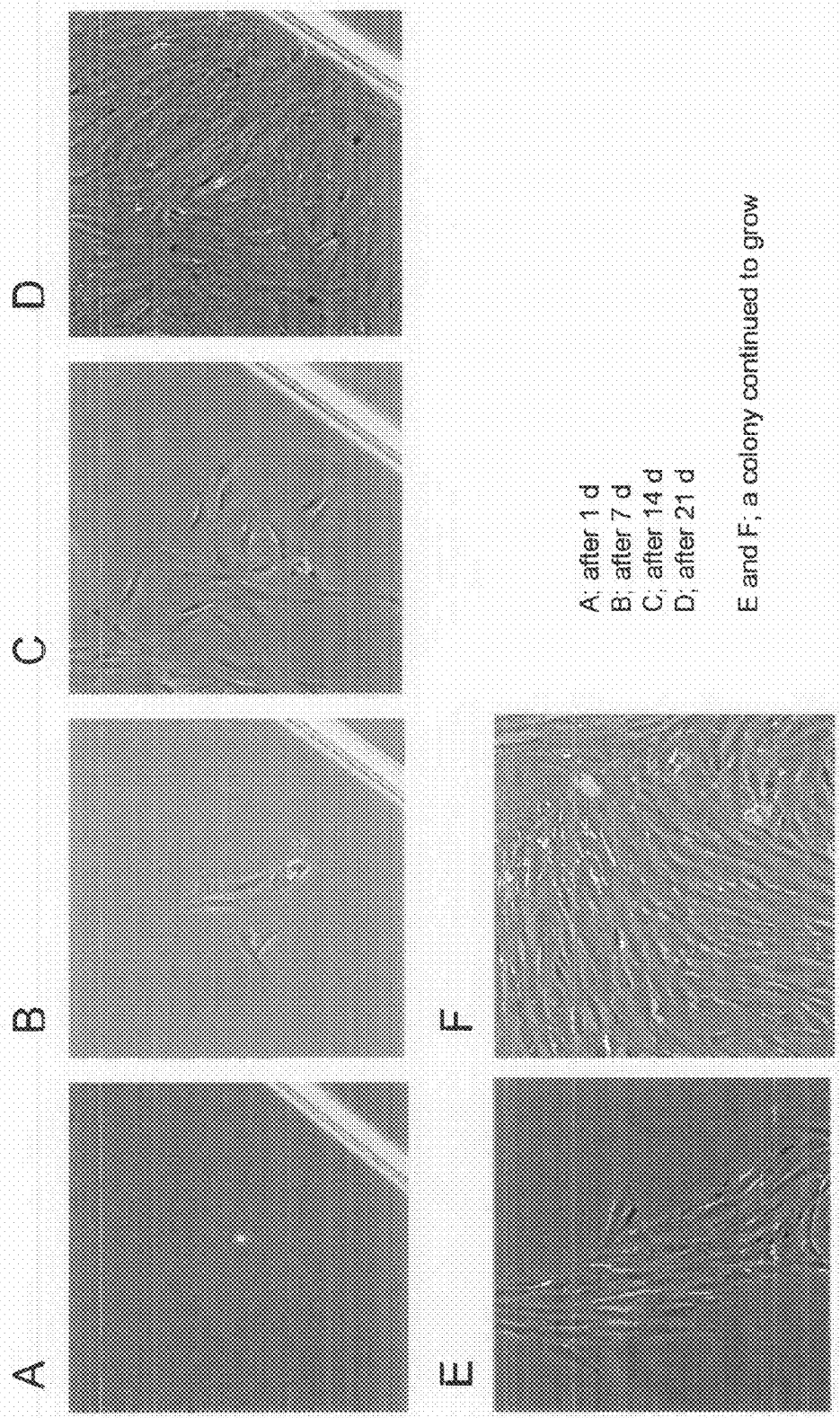
FIG. 12 shows a photograph of colony formation of the DP cell fractions.
Figure 13:
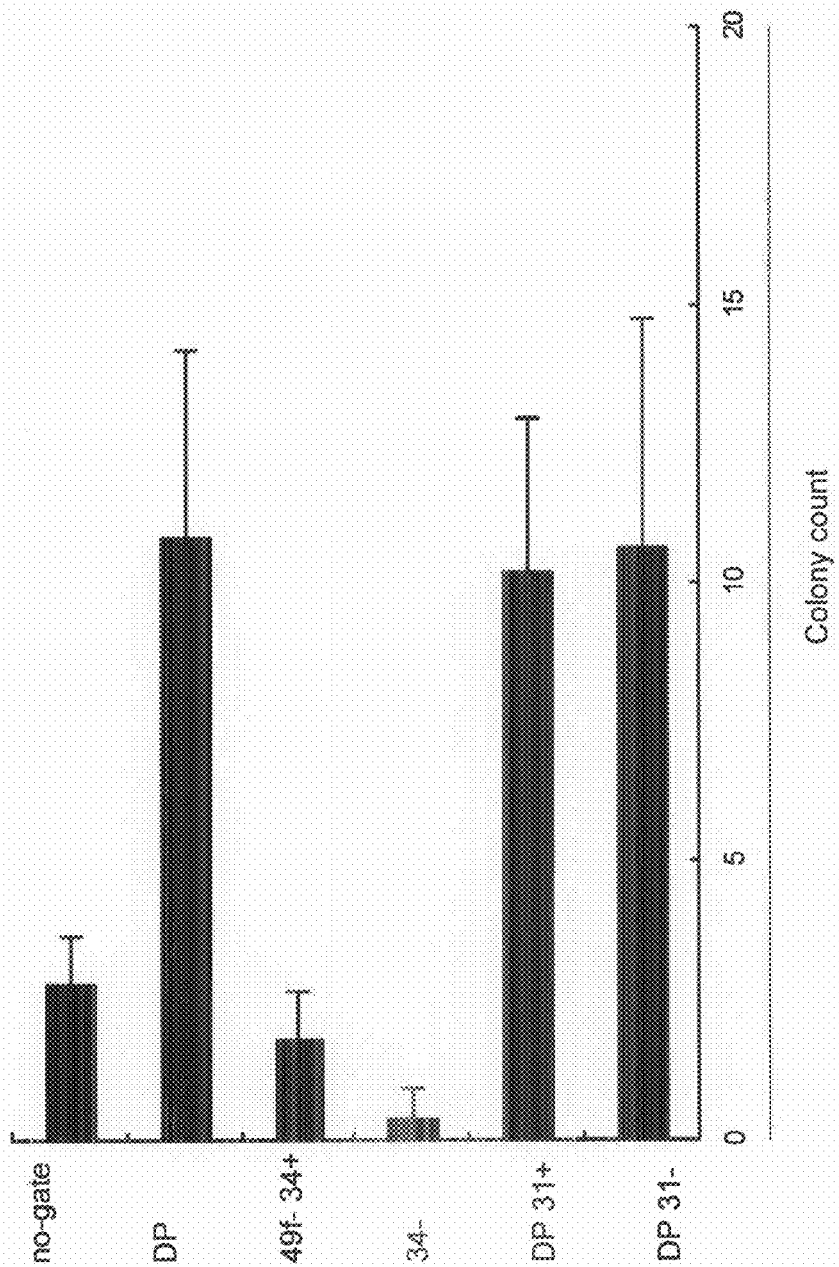
FIG. 13 shows the ability of the CD31(+) subfraction (DP31+) to form colony in the DP fraction, the CD49f(-)CD34(+) fraction, the CD34(-) fraction, and the DP fraction and the ability of the CD31 (-) subfraction (DP31-) to form colony in the DP fraction.

FIG. 12 shows colony-forming conditions of the DP cell fraction on day 1 (A), day 7 (B), day 14 (C), and day 21 (D). FIGS. 12E and 12F show the conditions of growing colonies. FIG. 13 shows the ability of the CD31(+) subfraction (DP31+) to form colony in the DP fraction, the CD49f(−)CD34(+) fraction, the CD34(−) fraction, and the DP fraction and the ability of the CD31 (−) subfraction (DP31−) to form colony in the DP fraction. As shown in the figures, the colony forming ability of the DP fraction was higher than that of other fractions (the CD49f(−)CD34(+) fraction and the CD34 (−) fraction). No difference in colony forming ability was observed between the CD31(+) subfraction and the CD31(−) subfraction in the DP fraction.

FIG. 14 shows the results of transplantation of the DP fraction into the uterus of a severely immunodeficient mouse. As shown in the figure, the vimentin-positive tissue; i.e., tissue (yellow) that was derived from a human (red), was αSMA positive (green), and had morphological features of uterine smooth muscle, appeared in the uterus into which the DP fraction had been transplanted. This indicates that the DP cell fraction has the ability to construct the uterine muscle-like tissue.

Thus, it was demonstrated that the uterine smooth muscle stem cells could be isolated using CD34 and CD49f expression as an indicator without performing selection using a lineage marker.

INDUSTRIAL APPLICABILITY

As described in the examples above, the DP/Lin− fraction of the present invention that is CD31-, CD45-, and Glycophorin A-negative and CD34- and CD49f-positive and the DP fraction of the present invention that is CD45-negative and CD34- and CD49f-positive have features of tissue stem cells, such as 1) an undifferentiated state, 2) multipotency, and 3) self-formation. Thus, DP/Lin− and DP were found to be uterine muscle tissue stem cells, and the method of the present invention succeeded in isolating tissue stem cells from uterine muscle for the first time in the world. The isolated DP/Lin− and DP fractions are biological resources that are useful in relation to cellular mechanism that is in charge of growth, degeneration, and functional expression of the uterine muscle at the timing of generation of uterine muscle, pregnancy, and childbirth. Further, they can be useful for analysis of the cause of disease arising from uterine muscle, such as hysteromyoma, or development of drugs for treating such diseases. Also, DP/Lin− and DP cells are expected to have clinical applications as cellular materials for treatment of other organs.

All publications, patents, and patent applications cited herein are incorporated herein by reference in their entirety.

The invention claimed is:

1. A method for isolating a population of uterine smooth muscle-derived stem cells from mammalian uterine smooth muscle, the method comprising:
   bringing the mammalian uterine smooth muscle cells dispersed from uterine smooth muscle into contact with an anti-CD34 antibody and an anti-CD49f antibody labeled with fluorescent dyes; and
   isolating a population of uterine smooth muscle-derived stem cells that bind to the anti-CD34 antibody and the anti-CD49f antibody.

2. A method for isolating a population of uterine smooth muscle-derived stem cells from mammalian uterine smooth muscle, the method comprising:
   bringing the mammalian uterine smooth muscle cells into contact with an anti-CD45 antibody, an anti-CD34 antibody, and an anti-CD49f antibody labeled with fluorescent dyes; and
   isolating a population of uterine smooth muscle-derived stem cells that do not bind to the anti-CD45 antibody but bind to the anti-CD34 antibody and the anti-CD49f antibody.

3. The method according to claim 1, further comprising sorting the mammalian uterine smooth muscle cells via flow cytometry.

4. A method for isolating a population of uterine smooth muscle-derived stem cells from mammalian smooth muscle, the method comprising:
   sorting the mammalian uterine smooth muscle cells into Lin (CD31, CD45, and Glycophorin A)-positive cells (Lin+) and Lin-negative cells (Lin−) via flow cytometry, isolating sampling the Lin-negative cells, and
   further isolating CD34-positive and CD49f-positive cells from the Lin-negative cells.

5. The method according to claim 1, further comprising isolating CD34-positive and CD49f-positive cells from the mammalian uterine smooth muscle cells via flow cytometry.

6. A method for isolating a population of uterine smooth muscle-derived stem cells from mammalian uterine smooth muscle, the method comprising:
   sampling CD45-negative cells from mammalian uterine smooth muscle via flow cytometry; and
   further isolating CD34-positive and CD49f-positive cells from the CD45-negative cells.

7. The method according to claim 1, wherein the mammalian uterine smooth muscle cells are human smooth muscle cells.

8. An isolated population of uterine smooth muscle-derived stem cells, which are CD31-, CD45-, and Glycophorin A-negative and CD34- and CD49f-positive and which are isolated by a method comprising
   sorting mammalian uterine smooth muscle cells obtained from mammalian uterine smooth muscle into Lin (CD31, CD45, and Glycophorin A)-positive cells (Lin+) and Lin-negative cells (Lin−) via flow cytometry, sampling the Lin-negative cells, and
   further isolating CD34-positive and CD49f-positive cells from the Lin-negative cells to obtain the population of uterine smooth muscle-derived stem cells that bind to the anti-CD-34 antibody and to the anti-CD49f antibody.

9. An isolated population of uterine smooth muscle-derived stem cells, which are CD34- and CD49f-positive and which are isolated by a method comprising bringing mammalian uterine smooth muscle cells dispersed from smooth muscle into contact with an anti-CD34 antibody and an anti-CD49f antibody labeled with fluorescent dyes; and isolating a population of uterine smooth muscle-derived stem cells that bind to the anti-CD34 antibody and the anti-CD49f antibody.

10. An isolated population of uterine smooth muscle-derived stem cells, which are CD45-negative and CD34- and CD49f-positive and which are isolated by a method comprising bringing mammalian uterine smooth muscle cells obtained from mammalian uterine smooth muscle into contact with an anti-CD45 antibody, an anti-CD34 antibody, and an anti-CD49f antibody labeled with fluorescent dyes; and isolating a population of uterine smooth muscle-derived stem cells that do not bind to the anti-CD45 antibody but bind to the anti-CD34 antibody and the anti-CD49f antibody.

11. The isolated population of uterine smooth muscle-derived stem cells according to claim 9, which are further ABCG2-positive.

12. The isolated population of uterine smooth muscle-derived stem cells according to claim 10, which differentiates into smooth muscle upon transplantation thereof to smooth muscle.

13. The isolated population of uterine smooth muscle-derived stem cells according to claim 12 derived from uterine muscle, which differentiates into uterine muscle upon transplantation thereof into uterine muscle.

14. A composition, comprising the isolated population of uterine smooth muscle-derived stem cells according to claim 9, suitable for regenerating smooth muscle tissue.

15. A method for isolating a population of uterine smooth muscle-derived stem cells from mammalian uterine smooth muscle, the method comprising:

bringing the mammalian uterine smooth muscle into contact with an anti-CD31 antibody, an anti-CD45 antibody, an anti-Glycophorin A antibody, an anti-CD34 antibody, and an anti-CD49f antibody labeled with fluorescent dyes; and isolating a population of uterine smooth muscle-derived stem cells that do not bind to the anti-CD31 antibody, the anti-CD45 antibody, and the anti-Glycophorin A antibody but bind to the anti-CD34 antibody and the anti-CD49f antibody.

16. A method for inducing differentiation of an isolated population of uterine smooth muscle-derived stem cell into fat cells, bone cells, or cartilage cells, the method comprising bringing mammalian uterine smooth muscle cells dispersed from smooth muscle into contact with an anti-CD34 antibody and an anti-CD49f antibody that are labeled with fluorescent dyes, isolating a population of uterine smooth muscle-derived stem cells that bind to the anti-CD34 antibody and the anti-CD49f antibody, and culturing the isolated population of uterine smooth muscle-derived stem cells in a medium suitable for inducing differentiation into fat cells, bone cells, or cartilage cells.

17. The method according to claim 16, wherein the isolated smooth muscle-derived stem cells are cultured in a fat cell differentiation medium, osteoblast differentiation medium or cartilage cell differentiation medium.

* * * * *